United States Patent [19]
Lavielle et al.

[11] Patent Number: 5,079,249
[45] Date of Patent: Jan. 7, 1992

[54] BIS(ARYL)ALKENE PYRROLIDINE COMPOUNDS

[75] Inventors: Gilbert Lavielle, La Celle Saint Cloud; Francis Colpaert, Le Vesinet; Michel Laubie, Vaucresson, all of France

[73] Assignee: Adir et Compagnie, Neuilly-sur-Seine, France

[21] Appl. No.: 572,858

[22] Filed: Aug. 24, 1990

Related U.S. Application Data

[62] Division of Ser. No. 460,751, Jan. 4, 1990.

[30] Foreign Application Priority Data

Jan. 10, 1989 [FR] France .................. 89 00213

[51] Int. Cl.$^5$ ............... A61K 31/53; C07D 487/12
[52] U.S. Cl. ................... 514/248; 514/256; 514/257; 514/258; 544/251; 544/252; 544/281; 544/295; 544/360; 544/363; 544/368; 544/569; 544/580; 544/342
[58] Field of Search ............ 544/237, 252, 281, 285, 544/295, 360, 363, 368, 369, 385, 392; 514/248, 250, 255, 258, 259

[56] References Cited

U.S. PATENT DOCUMENTS 4,540,780 9/1985 Downs et al. .............. 544/129
4,841,047 6/1989 Engel et al. .............. 540/599

FOREIGN PATENT DOCUMENTS 110435 9/1983 European Pat. Off.
181793 5/1986 European Pat. Off.
228893 7/1987 European Pat. Off.
235463 9/1987 European Pat. Off.
266246 5/1988 European Pat. Off.
2303246 1/1973 Fed. Rep. of Germany
2614021 4/1987 France

OTHER PUBLICATIONS

Lucki, J. Ph. Ex. Ther. (1984), 228, No. 1, pp. 133-139.
LeBars, D., Neuronal Serotonin (1988), John Wiley and Sons Ltd., N.Y., pp. 171-229.
Iversen, S. D., Neuropharmacol. (1984), 23, pp. 1553-1560.
Markianos, J., et al., Acta Neurol. Scand. (1982), 66, pp. 267-275.
Fozard, J. R., et al., TIPS (1989), 10, pp. 307-309.
Ceulemans DLS, Pharmacopsychiat., (1985), 18, pp. 303-305.
Anisman, H. et al., Behav. Brain. Scienc., (1982), 5, pp. 89-137.
Blier, P., et al., J. Clin. Psychopharmacol., (1987), 7, pp. 24S-35S.
Jacobs, B. L., et al., TINS, (1979) Nov. pp. 276-280.
Borison, R. L., et al., Comms. Psychopharmacol, (1978), 2, pp. 209-214.
CA, 111:164299r (1989).
CA, 112:66807f (1990).

Primary Examiner—Mukund J. Shah
Assistant Examiner—Jyothsna Venkat
Attorney, Agent, or Firm—Gordon W. Hueschen

[57] ABSTRACT

The invention relates to compounds of formula I:

$$R-(CH_2)_m-N\begin{array}{c}(CH_2)_n\\(CH_2)_p\end{array}(-CH)_q=C\begin{array}{c}R_1\\R_2\end{array} \quad (I)$$

in which
m = 2–4,
n and p, which may be identical or different, are an integer equal to 1, 2 or 3, with the proviso that the sum of n and p
q = 0 or 1,
R is a 1,2,3,4-tetrahydro-2,4-dioxo-3-quinazolinyl radical, optionally substituted, a 1,3,4,6,11,11a-hexahydro-1,3-dioxo-2H-pyrazino[1,2-b]isoquinol-2-yl radical, a 1,2-dihydro-1-oxo-2-phthalazinyl radical, optionally substituted, a 2,6-dioxo-1-piperazinyl radical of formula W:

$$R_3-CH_2-N\diagup\!\!\!\diagdown N- \quad (W)$$

($R_3$ is a 2-pyridyl radical or an optionally substituted phenyl radical),
a radical of formula Z:

(Z) structure with $R_4$, N, $CH_3$, OH ($R_4$ is a carbamoyl radical, a cyano radical, a hydroxycarbonyl radical or an alkoxycarbonyl radical having 1 to 6 carbon atoms),
or a radical of formula Y:

$$R_5-N\diagup\!\!\!\diagdown N- \quad (Y)$$

($R_5$ is a 2-pyrimidinyl radical, a 1-isoquinolyl radical, a 2-quinolyl radical, a 2-pyridyl radical, a benzyl radical, optionally substituted, a 2-thiazolyl radical, optionally substituted, or a 2-benzothiazolyl radical) and
either $R_1$ and $R_2$, identical or different, each are a substituted phenyl radical, or $R_1$ is a phenyl radical and $R_2$ a 2-pyridyl radical (it being possible for each of these two radicals to be substituted), or $R_1$ and $R_2$, together with the carbon atom to which they are attached, form a fluorene radical. These compounds are useful as Serotonin Antagonists.

10 Claims, No Drawings

BIS(ARYL)ALKENE PYRROLIDINE COMPOUNDS

This is a division of application Ser. No. 07/460,751, filed Jan. 4, 1990.

The present invention relates to new bis(aryl)alkene compounds, to processes for preparing them and to pharmaceutical compositions containing them.

Some 1-(morpholinylalkyl or -oxoalkyl)-, 1-(pyrrolidinylalkyl or -oxoalkyl)-, 1-(piperidylalkyl or -oxoalkyl)-, 1-(piperazinylalkyl or -oxoalkyl)-, 1-(perhydrothiazinylalkyl or -oxoalkyl)- or 1-(cyclohexenylalkyl or -oxoalkyl)-4-(diphenylmethylene)piperidine compounds having anticholinergic properties are already described U.S. Pat. Nos. 4,540,780, 4,584,301, 4,640,925, 4,666,905). 4-(Diphenylmethyl)- or 4-(diphenylmethylene)piperidine compounds substituted at the 1-position with olefins, alcohols, ketones or oximes are also known U.S. Pat. Nos. 4,180,583, 3,878,217, DE 2,303,305; DE 2,303,245; DE 2,303,246; 3,922,276). The latter compounds are endowed with antihistaminic, anti-allergic and bronchodilatory properties, or are anti-inflammatories and tranquillizers. Derivatives of 1-[(4-diphenylmethylene-1-piperidyl)alkyl]-2-benzimidazolone (Patent Application EP 181,793), of 3-[(4-diphenylmethylene-1-piperidyl)alkyl]imidazo[4,5-b]pyridin-2-one (Patent Application EP 266,246) or of [4-bis(aryl)methylene-1-piperidyl]alkylpyrimidinones (Patent Application EP 110,435) are known to be serotonin antagonists. Arylalkyl or arylalkene compounds of pyrrolidines, piperidines or homopiperidines, substituted on the nitrogen with side chains containing hetero atoms, are described in Patent Applications EP 228,893 and EP 235,463 as having cardiovascular, antihistaminic and antisecretory activities. 1-(1,1-Diphenyl-1-alkenyl)-piperazine derivatives having antidepressant properties are also known (Patent Application FR 87/05,311).

The compounds of the present invention, which are bis(aryl)alkene compounds of novel structure, possess exceptional pharmacological properties. In effect, they are serotonin antagonists at the 5-HT$_2$ level without an α$_1$-adrenolytic component. Furthermore, the compounds of the invention are capable of specifically antagonizing a complex symptom induced in animals by the injection of 5-hydroxytryptophan, which leads to the prediction that these new compounds are also serotonin antagonists at the 5-HT$_1$ type receptor level. The compounds of the invention are clearly distinguished from other bis(aryl)alkene compounds already described in the literature.

The subject of the present invention is, more especially, the bis(aryl)alkene compounds of formula I:

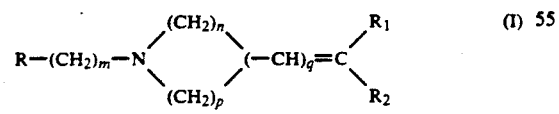

in which
m denotes an integer from 2 to 4,
n and p, which may be identical or different, denote an integer equal to 1, 2 or 3, with the proviso that the sum of n and p is not less than 3 and not more than 5,
q denotes 0 or 1,
R denotes a 1,2,3,4-tetrahydro-2,4-dioxo-3-quinazolinyl radical (optionally substituted on the benzene ring with one or more halogen atoms or with alkyl radicals having 1 to 6 carbon atoms or alkoxy radicals having 1 to 6 carbon atoms), a 1,3,4,6,11,11a-hexahydro-1,3-dioxo-2H-pyrazino[1,2-b]isoquinol-2-yl radical, a 1,2-dihydro-1-oxo-2-phthalazinyl radical (optionally substituted on the benzene ring with one or more halogen atoms or with alkyl radicals having 1 to 6 carbon atoms or alkoxy radicals having 1 to 6 carbon atoms), a 2,6-dioxo-1-piperazinyl radical of formula W:

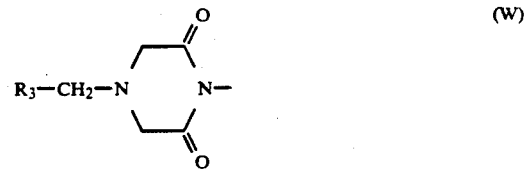

(in which R$_3$ denotes a 2-pyridyl radical or a phenyl radical optionally substituted with one or more halogen atoms or alkyl or alkoxy radicals having 1 to 6 carbon atoms),
a radical of formula Z:

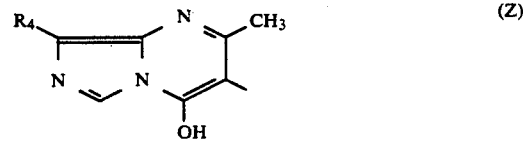

(in which R$_4$ denotes a carbamoyl radical, a cyano radical, a hydroxycarbonyl radical or an alkoxycarbonyl radical having 1 to 6 carbon atoms),
or a radical of formula Y:

(in which R$_5$ denotes a 2-pyrimidinyl radical, a 1-isoquinolyl radical, a 2-quinolyl radical, a 2-pyridyl radical, a benzyl radical—optionally substituted with an alkyl radical having 1 to 6 carbon atoms containing one or more halogen atoms, a 2-thiazolyl radical—optionally substituted with one or more alkyl radicals having 1 to 6 carbon atoms or with a phenyl radical, or a 2-benzothiazolyl radical), and
R$_1$ and R$_2$ either
identical or different, each denote a phenyl radical substituted with one or more halogen atoms or with one or more alkyl or alkoxy radicals containing 1 to 6 carbon atoms,
or
R$_1$ denotes a phenyl radical and R$_2$ a 2-pyridyl radical (it being possible for each of these two radicals to be substituted with one or more halogen atoms or with one or more alkyl or alkoxy radicals containing 1 to 6 carbon atoms),
or
R$_1$ and R$_2$, together with the carbon atom to which they are attached, form a fluorene radical, their possible stereoisomers and their addition salts with a pharmaceutically acceptable inorganic or organic acid.

The subject of the present invention is also a process for preparing compounds of general formula I, wherein: either
an amine of general formula II $$RH \quad (II)$$

in which R has the same meaning as for the formula I, is condensed with a compound of general formula III:

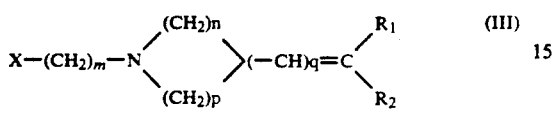

in which X denotes a halogen atom, a mesyloxy radical or a tosyloxy radical and m, n, p, q and $R_1$ and $R_2$ have the same meaning as above, to form the compounds of formula I,
or
an amine of formula IV:

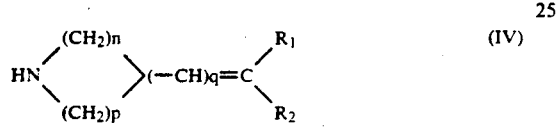

in which $R_1$, $R_2$, n, p and q have the same meaning as for the formula I, is condensed with a compound of formula V:

in which X, R and m have the same meaning as above, to form the compounds of formula I, or
a 4-aminoimidazole derivative is cyclized with a compound of formula VI:

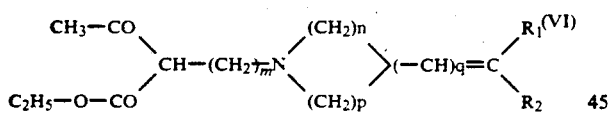

in which m, n, p, q, $R_1$ and $R_2$ have the same meaning given for the formula I,
to form the compounds of the formula I in which R comprises an imidazo[1,5-a]pyrimidine group and m, n, p, q, $R_1$ and $R_2$ have the meaning stated for the formula I, which compounds are then,
if so desired, separated into their possible stereoisomers and/or salified with a pharmaceutically acceptable organic or inorganic acid to form the corresponding addition salts.

Some compounds corresponding to the general formula II, such as, for example, 1-(2-pyrimidinyl)piperazine, 1-(2-pyridyl)piperazine and 4-amino-5-carbamoylimidazole, are commercial products (Aldrich ®). 1,3,4,6,11,11a-Hexahydro-2H-pyrazino[1,2-b]isoquinoline-1,3-dione, a compound also corresponding to the formula II, may be prepared by heating 3-carboxy-1,2,3,4-tetrahydro-2-isoquinolylacetic acid in formamide. This latter compound is prepared by the action of 2-chloroacetic acid on 1,2,3,4-tetrahydro-3-isoquinolinecarboxylic acid. 1-(2-Quinolyl)piperazine is obtained as described in U.S. Pat. No. 3,743,732. 1-(1-Isoquinolyl)piperazine is obtained as described in U.S. Pat. No. 3,932,412.

The compounds of formula V are obtained by treating the compounds of general formula II, either with a bromochloroalkane of formula VII:

$$Br(CH_2)_mCl \quad (VII)$$

in which m has the same meaning as for the formula I, or with halohydrins of formula VIII:

$$Hal(CH_2)_mOH \quad (VIII)$$

in which m has the same meaning as for the formula I and Hal denotes a halogen atom. The alcohols thereby obtained are then converted to derivatives of formula V by conventional methods.

The amines of formula IV corresponding to the amines $IV_a$–$IV_d$.

The amines of formula $IV_a$:

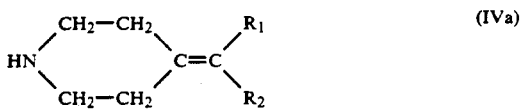

in which $R_1$ and $R_2$ have the same meaning as for the formula I, are prepared from 1-alkylpiperidine derivatives halogenated at the 4-position and ketones of formula IX:

in which $R_1$ and $R_2$ have the same meaning as for the formula I, in the presence of magnesium, according to known processes (Grignard reaction). The tertiary alcohols derived from this reaction are then subjected to a dehydration. The 4-bis(aryl)methylene-1-alkylpiperidines thereby obtained are then dealkylated by conventional processes.

The amines of formula $IV_b$:

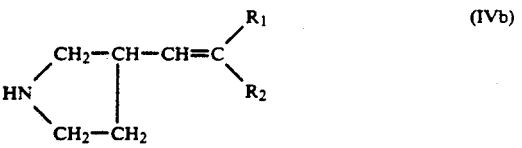

in which $R_1$ and $R_2$ have the meaning stated for the formula I, are prepared from (1-benzyl-3-pyrrolidinyl)acetonitrile, which is converted to ethyl 2-(1-benzyl-3-pyrrolidinyl)acetate. This compound is then subjected to the action of arylmagnesium halides, and the tertiary alcohols derived from the reaction give, after dehydration and dealkylation, the expected secondary amines.

The compounds of formula $IV_c$:

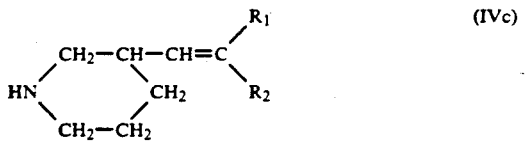

in which $R_1$ and $R_2$ have the meaning stated for the formula I, are prepared from 3-chloromethyl-1-methylpiperidine. This compound is converted by conventional methods to (1-methyl-3-piperidyl)-methylmagnesium chloride. The latter is then condensed with a ketone of formula IX to form 2-(1-methyl-3-piperidyl)-1,1-bis(aryl)ethanol compounds which, after dehydration and demethylation, give the compounds of formula $IV_c$.

The amines of formula $IV_d$:

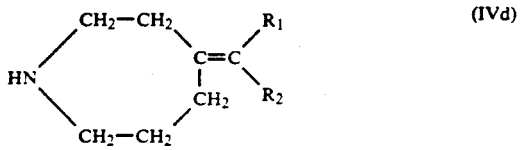

in which $R_1$ and $R_2$ have the meaning stated for the formula I, are prepared from 4-(N,N-dimethylamino)butyronitrile. This compound is condensed with 3-chloro-1-iodopropane to form 2-[2-(N,N-dimethylamino)ethyl]-5-chloropentanenitrile which, after cyclization, gives 4-cyano-1-methylperhydroazepine. The amines of formula $IV_d$ are synthesized from this nitrile according to the process described for the derivatives $IV_b$.

The compounds of formula III are prepared by treating the amines of formula IV, either with bromochloroalkanes of formula VII, or with halohydrins of formula VIII, which give, in a first step, alcohols which can be converted to compounds of formula III by conventional methods.

The compounds of formula VI are prepared by condensation of the compounds of formula III with ethyl acetoacetate (Ann. Rep. Sankyo Res. Lab., (1977), 29, p. 75-98).

The condensation of the amines of formula II or IV with the compounds of formula III or V is carried out in a polar organic solvent in the presence of inorganic salts such as sodium carbonate and sodium iodide, at a temperature of between 40° C. and 100° C.

The cyclization of 4-amino-5-carbamoylimidazole with the compounds of formula VI is performed in the heated state and in the presence of phosphoric acid.

Among pharmaceutically acceptable acids for the preparation of addition salts with the compounds of general formula I, hydrochloric, phosphoric, fumaric, citric, oxalic, sulfuric, ascorbic, tartaric, maleic, mandelic and methanesulfonic acids, and the like, may be mentioned.

The compounds of the present invention possess highly advantageous pharmacological properties. In effect, they were subjected to various pharmacological tests which showed their histamine-and serotoninantagonist activities at the 5-$HT_2$ receptor level, without an $\alpha_1$-adrenolytic component. The compounds of the invention are also potent inhibitors of the complex and characteristic symptoms induced in animals by the injection of 5-hydroxytryptophan. The compounds of the present invention are hence also serotonin antagonists at the 5-$HT_1$ type receptor level (J. Ph. Ex. Ther., (1984), 228, No. 1, p. 133-139). The in vivo tests also demonstrated that the compounds of the invention are very well absorbed orally, which constitutes a considerable advantage when they are applied in therapy.

The antihistaminic properties of the compounds of the invention enable them to be used as anti-allergic and antipruritic agents, for treatment of the airways such as rhinitis and hayfever, and for the treatment of asthma and Quincke's edema.

The compounds of the invention which are more specifically active as antagonists at serotonin receptors at central level, and most especially 5-$HT_2$ and 5-$HT_1$ receptors, may be used for counteracting certain adverse effects of these mediators. They find application more especially in anxiety and dysthymia (Ceulemans DLS, Hoppenbrouwers M. L., Gelders Y. G. and Reyntjens A. J. M., Pharmacopsychiat., (1985), 18, p. 303-305 and Le Bars, Neuronal Serotonin Eds Osborne, NN and Hamon M., John Wiley and Sons Ltd, N.Y., (1988), p. 171-229), in depression and stress (Anisman H and Zacharko R. M., Behav. Brain. Scienc., (1982), 5, p. 89-137 and Blier P., de Montigny C. and Chaput Y., J. Clin. Psychopharmacol., (1987), 7, p. 245-335), pain (Jacobs B. L. and Trulson M. E., TINS, (1979) Novem., p. 276-280), memory disorders (Markianos M., Hadjikonstantinou and Bistolaki E., Acta Neurol. Scand., (1982), 66, p. 267-275), Parkinson disease (Le Bars, Neuronal Serotonin Eds. Osborne NN and Hamon M, John Wiley and Sons Ltd. N.Y., (1988), p. 171-229) and schizophrenia (Borison R. L., Havdala H. S. and Diamond B. I., Comms. Psychopharmacol., (1978), 2, p. 209-214 and Iversen S. D., Neuropharmacol., (1984), 23, p. 1553-1560) and migraine (Fozard J. R. and Gray J. A., TIPS, (1989), 10, p. 307-309).

The invention also covers pharmaceutical compositions containing, as active principle, at least one compound of general formula I, or one of its salts with a pharmaceutically compatible inorganic or organic acid, in combination with one or more suitable inert excipients.

The pharmaceutical compositions thereby contained are advantageously presented in various forms such as, for example, tablets, dragées, hard gelatin capsules, suppositories, injectable solutions or solutions to be taken by mouth.

The dosage can vary widely in accordance with the patient's age and weight and the nature and severity of the disease, as well as the administration route. Generally speaking, the unit dosage will range between 0.5 and 100 mg and the daily dosage, useable in human therapy, between 0.5 mg and 300 mg.

The preferred administration route is the oral or parenteral route.

The examples which follow, given without implied limitation, illustrate the invention.

The melting points were measured according to the micro-Kofler technique.

The proton nuclear magnetic resonance ($^1H$ NMR) or carbon-13 nuclear magnetic resonance ($^{13}C$ NMR) spectra of the compounds of general formula I were recorded, depending on the case, at 60, 200 and 400 MHz, and are indicated in Table I.

EXAMPLE 1

3-{2-[4-]Bis(4-fluorophenyl)methylene]piperidino]ethyl}-8-carbamoyl-4-hydroxy-2-methylimidazo[1,5-a]pyrimidine hydrochloride

STAGE A

4-[Bis(4-fluorophenyl)methylene]-1-(chloroethyl)-piperidine hydrochloride 0.31 mol of ethylene oxide is dissolved in a solution of 0.28 mol of 4-[bis(4-fluorophenyl)methylene]piperidine (prepared according to the process described in U.S. Pat. No. 3,922,276) in one liter of anhydrous methanol at −10° C., and the reaction is completed by stirring for 15 hours at −20° C. and then for 3 hours at 45° C. The mixture is concentrated under vacuum. The product is purified by chromatography on 140 g of 230–400 mesh silica using a mixture of dichloromethane and methanol (95:5 V/V) as eluent. The oil obtained is solubilized in one liter of anhydrous toluene and 0.27 mol of thionyl chloride is then added. The mixture is brought to reflux for 30 min to complete the reaction. The mixture is cooled to 20° C. and the precipitate formed is filtered off.

Yield: 90%.

Proton nuclear magnetic resonance spectrum (200 MHz, solvent $CDCl_3$): 2.5–3.3 ppm, m, 6H; 3.4 ppm, t, 2H; 3.5–3.9 ppm, m, 2H; 4.1 ppm, t, 2H; 6.8–7.4 ppm, m, 8H.

STAGE B

Ethyl 2-acetyl-4-{4-[bis(4-fluorophenyl)methylene]-piperidino}butyrate 0.182 mol of ethyl acetoacetate is added at 0° C. to a suspension containing 0.182 mol of sodium hydride in 800 ml of tetrahydrofuran. The reaction medium is maintained for one hour at 20° C. and 0.182 mol of sodium iodide is then added. The mixture is cooled to 0° C. and 0.182 mol of 4-[bis(4-fluorophenyl)methylene]-1-(chloroethyl)piperidine is added. The mixture is brought to reflux for 12 hours and then concentrated under vacuum. The residue is taken up in water and the product is extracted with dichloromethane. The oil obtained is purified by chromatography on a column of 70–230 mesh silica, eluting with a mixture of dichloromethane and methanol (99:1 V/V).

Yield: 38%.

Proton nuclear magnetic resonance spectrum (200 MHz, solvent $CDCl_3$): 1.8–2.1 ppm, m, 2H; 1.2–1.4 ppm, t, 3H; 2.3 ppm, s, 3H; 2.05 ppm, t, 2H; 2.2–2.6 ppm, m, 8H; 3.55 ppm, t, 1H; 4.1–4.3 ppm, q, 2H; 6.8–7.2 ppm, m, 2H.

STAGE C 0.01 mol of 4-amino-5-carbamoylimidazole hydrochloride, 0.011 mol of the ester prepared in the preceding step and 10.5 g of phosphoric acid are mixed. The mixture is brought to 80° C. for 30 minutes.

The mixture is hydrolyzed with ice and neutralized with concentrated sodium hydroxide to obtain the precipitation of 4-{2-[4-]bis(2-fluorophenyl)methylene]-piperidino]ethyl}-8-carbamoyl-4-hydroxy-2-methylimidazo[1,5-a]pyrimidine. The product is then salified with ethanolic hydrogen chloride.

Yield: 30%.

Melting point: >260° C.

EXAMPLE 2

2-{2-[4-[(4Fluorophenyl)phenylmethylene]-piperidino]ethyl}-1,3,4,6,11,11a-hexahydro-1,3-dioxo-2H-pyrazino[1,2-b]-isoquinoline dihydrochloride A mixture containing 0.0247 mol of 2-(2-chloroethyl)-1,3,4,6,11,11a-hexahydro-1,3-dioxo-2H-pyrazino[1,2-b]isoquinoline, 0.0235 mol of 4-[(4-fluorophenyl)phenylmethylene]piperidine, 5 g of sodium carbonate and 0.5 g of sodium iodide in 200 ml of methyl ethyl ketone is brought to reflux for 24 hours. After evaporation of the solvent, the residue is taken up in water and the product is extracted with benzene. The organic phase is dried over anhydrous sodium sulfate and concentrated under vacuum. The oil obtained is purified by chromatography on a column containing 150 g of silica (70–230 mesh). The product is eluted using a mixture of dichloromethane and ethanol (99:1 V/V).

The purified oil is converted to a dihydrochloride in ethanolic hydrogen chloride.

Yield: 37%.

Melting point: 150° C.

EXAMPLE 3

8-Carbamoyl-3-{2-[4-[(4-fluorophenyl)phenylmethylene]piperidino]ethyl}-4-hydroxy-2-methylimidazo[1,5-a]pyrimidine hydrochloride

STAGE A

8-Carbamoyl-4-hydroxy-3-hydroxyethyl-2-methylimidazo[1,5-a]pyrimidine 3 g of 4-amino-5-carbamoylimidazole hydrochloride, 1.51 g of sodium acetate, 1.69 g of ethanol, 7 g of 3-acetyltetrahydro-3-furanone and 45 ml of toluene are introduced successively into a 3-necked flask. The mixture is heated to reflux for 90 h. After cooling, the precipitate formed is taken up with boiling ethanol. The mixture is filtered and the residue is taken up in boiling water, the mixture is filtered and the residue is washed with ethanol and then dried.

Yield: 62%.

Proton nuclear magnetic resonance spectrum (400 MHz, solvent $DMSO-d_6$): 2.5 ppm, s, 3H; 2.6 ppm, t, 2H; 3.5 ppm, q, 2H; 4.6 ppm, t, 1H; 7.1–7.4 ppm, m, 2H; 8.1 ppm, s, 1H; 11.4 ppm, m, 1H.

STAGE B 0.0061 mol of the compound obtained in the preceding stage is added portionwise at room temperature to a suspension of 0.012 mol of sodium hydride in 80 ml of dimethylformamide. To the solution obtained, a solution containing 0.012 mol of (phenylmethylamino)triphenylphosphonium iodide (H. Zimmer and F. Singh, J. Org. Chem., (1963), 28, p 483) and 0.015 mol of 4-[(4-fluorophenyl)phenylmethylene]piperidine in 40 ml of dimethylformamide is added. The mixture is brought to 80° C. for 40 hours, the dimethylformamide is then evaporated off under vacuum and the residue is taken up in water. The product is extracted with chloroform. The oil obtained after concentration is purified by chromatography on silica (70–230 mesh) using a mixture of dichloromethane, methanol and ammonia solution (90:10:0.2 V/V/V) as eluent.

8-Carbamoyl-3-{2-[4-[(4-fluorophenyl)phenylmethylene]piperidino]ethyl}-4-hydroxy-2-methylimidazo[1,5-a]-pyrimidine hydrochloride is obtained after adding ethanolic hydrogen chloride to the purified base.

EXAMPLE 4

8-Cyano-3-{2-[4-[(4-fluorophenyl)phenylmethylene]-piperidino]ethyl}-4-hydroxy-2-methylimidazo[1,5-a]-pyrimidine hydrochloride

STAGE A

3-Chloroethyl-8-cyano-4-hydroxy-2-methylimidazo[1,5-a]pyrimidine 0.17 mol of the compound obtained in Stage A of Example 3, dissolved in 200 ml of phosphorus oxychloride, is brought to 85° C. for one hour 30 minutes. The phosphorus oxychloride is then removed by evaporation under vacuum. 100 ml of water are added and the pH is adjusted to 7 using sodium bicarbonate to crystallize the expected compound. The latter is filtered off.

Yield: 88%.

Melting point: 225° C.

Proton nuclear magnetic resonance spectrum (60 MHz, solvent DMSO-$d_6$): 2.45 ppm, s, 3H; 2.9 ppm, t, 2H; 3.7 ppm, t, 2H; 8.15 ppm, s, 1H; 13–13.4 ppm, 1H exchangeable.

STAGE B

A mixture containing 0.0046 mol of 4-[(4-fluorophenyl)phenylmethylene]piperidine, 0.0055 mol of the compound obtained in Stage A, 0.028 mol of sodium carbonate and 0.1 g of potassium iodide in 100 ml of 4-methyl-2-pentanone is brought to reflux for 8 hours. The mixture is concentrated under vacuum. The residue is taken up in water and the product is extracted with dichloromethane. After evaporation of the solvent, the product is solubilized in a mixture of ethyl ether and acetone and converted to a hydrochloride after the addition of hydrochloric acid. The salt is recrystallized in acetone.

Yield: 45%.

Melting point: 213°–215° C.

EXAMPLE 5

4-(2-Fluorobenzyl)-1-{3-[4-[(4-fluorophenyl)phenylmethylene]piperidono]propyl}-2,6-piperazinedione hydrochloride 0.0112 mol of 4-(2-fluorobenzyl)-2,6-piperazine-dione is added at 20° C. to a suspension of 0.0112 mol of sodium hydride in 40 ml of dimethylformamide. The mixture is brought to 60° C. for 45 minutes and then, at 20° C., 0.013 mol of 1-(3-chloropropyl)-4-[(4-fluorophenyl)phenylmethylene]piperidine is added. After 15 hours' stirring ar 20° C., the solvent is evaporated off under vacuum. The residue is taken up in water and the product is extracted with dichloromethane. The oil obtained is purified by chromatography on 520 g of silica (230–400 mesh), eluting with a mixture of dichloromethane and ethanol (98:2 V/V).

4-(2-Fluorobenzyl)-1-{3-[4-[(4-fluorophenyl)phenylmethylene]piperidino]propyl}-2,6-piperazinedione hydrochloride is obtained after the addition of ethanolic hydrogen chloride and recrystallization in a mixture of acetone and ethyl ether.

Yield: 26%.

Melting point: 199° C.

EXAMPLE 6

1-{3-[4-(9-Fluorenylidenyl)piperidino]propyl}-4-(2-fluorobenzyl)-2,6-piperazinedione hydrochloride

STAGE A 4-(9-Hydroxy-9-fluorenyl)-1-methylpiperidine

A solution of 0.412 mol of fluorenone in 300 ml of tetrahydrofuran is added at 20° C. to a solution of 0.659 mol of (1-methyl-4-piperidyl)magnesium chloride in 600 ml of tetrahydrofuran. The mixture is left stirring overnight and then hydrolyzed in the cold state with ammonium chloride solution. The reaction medium is concentrated and the residue is taken up in one liter of water. The product is extracted with chloroform. The organic phase is dried over anhydrous sodium sulfate and then concentrated. After crystallization of the expected product, the latter is washed with ethyl ether and filtered off.

Yield: 50%.

Melting point: 218° C.

Proton nuclear magnetic resonance spectrum (60 MHz, solvent $CDCl_3$): 1.0–3.0 ppm, m, 9H; 2,1 ppm, s, 3H; 4.7–5.8 ppm, 1H exchangeable; 7.2–8.0 ppm, m, 8H.

STAGE B 4-(9-Fluorenylidenyl)-1-methylpiperidine

A mixture containing 0.258 mol of the alcohol obtained in the preceding stage, 740 ml of glacial acetic acid and 220 ml of concentrated hydrochloric acid is brought to reflux for 12 hours. The reaction medium is then concentrated under vacuum, neutralized with 10N sodium hydroxide and extracted with dichloromethane and the solvent is evaporated off. The product crystallizes. The crystals are taken up with isopropyl ether.

Yield: 47%.

Melting point: 115° C.

Proton nuclear magnetic resonance spectrum (60 MHz, solvent $CDCl_3$): 2.3 ppm, s, 3H; 3.1–3.4 ppm, t, 4H; 3.4–3.7 ppm, t, 4H; 7.2–7.6 ppm, m, 4H; 7.6–8.1 ppm, m, 4H.

STAGE C

1-Ethoxycarbonyl-4-(9-fluorenylidenyl)piperidine 0.169 mol of the compound obtained in Stage B is dissolved in one liter of anhydrous toluene, 0.676 mol of ethyl chloroformate is added and the mixture is brought to reflux for 3 hours. The solvent is concentrated under vacuum. The crystallized product is taken up with isopropyl ether.

Yield: 70%.

Melting point: 124° C.

Proton nuclear magnetic resonance spectrum (60 MHz, solvent $CDCl_3$): 1.2–1.5 ppm, t, 3H; 3.2–3.6 ppm, t, 4H; 3.6–4.0 ppm, t, 4H; 4.1–4.5 ppm, q, 2H; 7.3–7.6 ppm, m, 4H; 7.6–8.1 ppm, m, 4H.

STAGE D 4-(9-Fluorenylidenyl)piperidine hydrochloride

A mixture of 0.01 mol of the compound obtained in the preceding stage and 0.012 mol of iodotrimethylsilane in 4.2 ml of chloroform is brought to 60° C. for one hour. The precipitate obtained is then filtered off under argon, washed with chloroform and dissolved in 50 ml of anhydrous methanol. 0.015 mol of sodium is added and the methanol is evaporated off. The residue is taken up in ethyl ether and dichloromethane. The mixture is filtered and methanolic hydrogen chloride is added to the filtrate to obtain the expected product in the form of a white precipitate.

Yield: 85%.

Melting point: >260° C.

STAGE E

A mixture of 0.6 g of potassium carbonate, 0.0044 mol of the compound prepared in Stage D and 0.0044 mol of 1-(3-chloropropyl)-4-(2-fluorobenzyl)-2,6-piperazinedione in 40 ml of 4-methyl-2-pentanone is brought to reflux for three hours. The mixture is then concentrated, the residue is taken up in 50 ml of water, the product is extracted with dichloromethane and the organic phase is dried and concentrated. The oil obtained is purified by chromatography on a column containing 100 g of silica (70–230 mesh) using a mixture of dichloromethane and ethanol (99:1 V/V) as eluent. 1-{3-[4-(9-Fluorenylidenyl)piperidino]propyl}-4-(2-fluorobenzyl)-2,6-piperazinedione hydrochloride is then formed using ethanolic hydrogen chloride.

Yield: 42%.

Melting point: 206° C.

EXAMPLE 7

1-{3-[4-[Bis(4-fluorophenyl)methylene]piperidino]-propyl}-4-(2-pyrimidinyl)piperazine dihydrochloride A mixture of 0.89 g of 1-(3-chloropropyl)-4-(2-pyrimidinyl)piperazine, 0.80 g of 4-[bis(4-fluorophenyl)methylene]piperidine and 0.51 g of potassium carbonate in 30 ml of 4-methyl-2-pentanone is brought to reflux for 48 hours in the presence of a trace of potassium iodide. The solvent is evaporated off and the residue is taken up in dichloromethane. The solution is washed with water. It is concentrated. The residue obtained is purified on a silica column using a mixture of dichloromethane and methanol (80:20 V/V) as eluent.

1.1 g of oil is obtained, which is converted to a dihydrochloride in ethanolic hydrogen chloride.

Yield: 69%.

Melting point: 204° C.

EXAMPLE 8

1-{3-[3-[2,2-Bis(4-fluorophenyl)vinylene]-1-pyrrolidinyl]propyl}-4-(2-fluorobenzyl)-2,6-piperazinedione dihydrochloride

STAGE A

Ethyl 2-(1-benzyl-2-pyrrolidinyl)acetate 120 g of 98% strength sulfuric acid are added dropwise to 0.299 mol of (1-benzyl-3-pyrrolidinyl)acetonitrile (Chem. Pharm. Bull., (1977), 25, (8), p. 1911–1922) in 150 ml of 95% strength ethanol. The mixture is then brought to reflux for 6 hours, the whole is cooled to 10° C. and 600 g of ice are added. The mixture is neutralized with sodium carbonate, the product is extracted with ethyl ether and the organic phase is dried over sodium sulfate and concentrated. The residue is then distilled under vacuum to obtain the expected ester.

Yield: 73%.

Boiling point: 115°–125° C. at 0.02 mmHg.

Proton nuclear magnetic resonance spectrum (200 MHz, solvent $CDCl_3$): 1.1–1.3 ppm, t, 3H; 1.3–1.5 ppm, m, 1H; 1.9–2.2 ppm, m+m, 1+1H; 2.4 ppm, d, 2H; 2.4–2.7 ppm, m, 3H; 2.7–2.9 ppm, d, 1H; 3.6 ppm, s, 2H; 4–4.2 ppm, q, 2H; 7.1–7.4 ppm, m, 5H.

STAGE B

1-Benzyl-3-[2,2-bis(4-fluorophenyl)-2-hydroxyethyl]-pyrrolidine

A solution of 0.946 mol of 4-bromofluorobenzene in 500 ml of tetrahydrofuran is added to 0.875 mol of magnesium in 60 ml of tetrahydrofuran. The mixture is brought to reflux for 3 hours. It is cooled to 10° C. and a solution of 0.218 mol of the compound obtained in the preceding stage in 150 ml of tetrahydrofuran is added. The mixture is brought to reflux for 20 hours and then hydrolyzed in the cold state with ammonium chloride solution. The mixture is diluted with one liter of water and extracted with dichloromethane. An excess of ethanolic hydrogen chloride is added to the organic phase, followed by one liter of ethyl ether. The mixture is filtered and the base is liberated to obtain the expected alcohol.

Yield: 77%.

Proton nuclear magnetic resonance spectrum (60 MHz, solvent $CDCl_3$): 1.0–3.1 ppm, m, 9H; 3.5 ppm, s, 2H; 3.4–3.9 ppm, 1H exchangeable; 6.6–7.7 ppm, m, 8H; 7.3 ppm, s, 5H.

STAGE C

1-Benzyl-3-[2,2-bis(4-fluorophenyl)vinylene]pyrrolidine

A mixture of 0.169 mol of the compound obtained in Stage B, 460 ml of acetic acid and 145 ml of 35% strength hydrochloric acid is brought to reflux for 4 hours. The acetic acid is then concentrated under vacuum, 400 ml of water and 400 ml of dichloromethane are added to the residue and the mixture is neutralized with sodium hydroxide. Concentration of the organic phase gives 60 g of an oil, which is purified by column chromatography using 800 g of silica (70–230 mesh) and, as eluent, a mixture of dichloromethane, methanol and ammonia solution (99:1:0.1 V/V/V). The expected product is obtained pure.

Yield: 80%.

Proton nuclear magnetic resonance spectrum (200 MHz, solvent $CDCl_3$): 1.5–1.8 ppm, m, 2H; 1.8–2.1 ppm, m, 1H; 2.3 ppm, d, 1H; 2.4–3.0 ppm, m, 3H; 3.5–3.7 ppm, d, 2H; 5.95 ppm, d, 1H; 6.7–7.4 ppm, m, 13H.

STAGE D

3-[2,2-Bis(4-fluorophenyl)vinylene]-1-(ethoxycarbonyl)pyrrolidine 0.136 mol of the compound obtained in Stage C is mixed with 0.272 mol of ethyl chloroformate and 600 ml of toluene. The mixture is heated to 100° C. for 4 hours and then cooled to 15° C. The organic phase is washed with 1N hydrochloric acid, dried over anhydrous sodium sulfate and concentrated under vacuum. The oil obtained is used without purification in the next step.

STAGE E 1,1-Bis(4-fluorophenyl)-2-(3-pyrrolidinyl)vinyl

A mixture of 0.014 mol of the oil obtained in Stage D and 25 ml of 48% strength hydrobromic acid is brought to reflux for three hours and then cooled, and the aqueous phase is washed with ethyl ether and neutralized with 2N sodium hydroxide. The aqueous phase is extracted with ethyl ether and concentrated. The oil obtained is purified by chromatography on a column containing 50 g of silica (70–230 mesh) using a mixture of dichloromethane and methanol (98:2 V/V) as eluent.

Yield: 48%

Proton nuclear magnetic resonance spectrum (60 MHz, solvent DMSO-d$_6$): 1.8–2.2 ppm, m, 2H; 2.6–3.5 ppm, m+m, 1H+4H; 6.2 ppm, d, 1H; 7.2–7.6 ppm, m, 8H; 9–10 ppm, 2H exchangeable.

STAGE F

A mixture of 0.017 mol of 1-(3-chloropropyl)-4-(2-fluorobenzyl)-2,6-piperazinedione, 3.4 g of sodium carbonate, 0.015 mol of the compound obtained in Stage E and 100 ml of 4-methyl-2-pentanone is brought to reflux for 8 hours. The reaction mixture is concentrated, 100 ml of distilled water are added and the mixture is extracted with 300 ml of dichloromethane. The oil obtained after concentration of the solvent is purified on a chromatographic column containing 350 g of silica (70–230 mesh) using a mixture of dichloromethane and methanol (99:1 V/V) as eluent.

Yield: 30%.

To form a 1-{3-[3-[2,2-bis(4-fluorophenyl)vinylene]-1-pyrrolidinyl]propyl}-4-(2-fluorobenzyl)-2,6-piperazinedione dihydrochloride, the base is dissolved in a mixture of acetone and ethyl ether and two equivalents of ethanolic hydrogen chloride are added. The mixture is concentrated and the product is precipitated using ethyl ether, filtered off and dried under vacuum.

Melting point: 160° C.

EXAMPLE 9

8-Carbamoyl-3-{3-[4-[(4-fluorophenyl)phenylmethylene]piperidino]propyl}-4-hydroxy-2-methylimidazo[1,5-a]pyrimidine hydrochloride

STAGE A

Ethyl 2-acetyl-5-{4-[(4-fluorophenyl)phenylmethylene]-piperidino}pentanoate 0.019 mol of 4-[(4-fluorophenyl)phenylmethylene]-piperidine, 0.019 mol of ethyl 3-acetyl-5-chloropentanoate, blocked in cyclic form (Chem. Ber. (1967), 100, p. 1675–1679), and 2.03 g of sodium carbonate in 80 ml of 2-butanone are brought to reflux. After evaporation of the solvent, the residue is taken up in water and extracted with dichloromethane. Deprotection is then performed according to the method described in Chem. Ber. (1967), 100, p. 1675–1679.

Yield: 40%.

Proton nuclear magnetic resonance spectrum (60 MHz, solvent CDCl$_3$): 1.1–1.4 ppm, t, 3H; 1.2–2.1 ppm, m, 4H; 2.25 ppm, s, 3H; 2.0–3.0 ppm, m, 10H; 3.3–3.7 ppm, t, 1H; 4.0–4.5 ppm, q, 2H; 7.0–7.6 ppm, m, 9H.

STAGE B

8-Carbamoyl-3-{3-[4-[(4-fluorophenyl)phenylmethylene]piperidino]propyl}-4-hydroxy-2-methylimidazo[1,5-a]pyrimidine hydrochloride is prepared by condensing 4-amino-5-carbamoylimidazole with the compound obtained in the preceding stage, according to the process described in Example 1, Stage C.

Yield: 30%.

Melting point: 245° C.

EXAMPLE 10

1-{3-[4-[(4-Fluorophenyl)phenylmethylene]piperidino]propyl}-4-(2-pyridylmethyl)-2,6-piperazinedione dihydrochloride This compound was prepared from 4-[(4-fluorophenyl)phenylmethylene]piperidine and 1-(3-chloropropyl)-4-(2-pyridylmethyl)-2,6-piperazinedione according to the process described in Example 6, Stage E.

Yield: 35%.

Melting point: 145° C.

EXAMPLE 11

3-{2-[4-[Bis(4-fluorophenyl)methylene]piperidino]ethyl}-8-cyano-4-hydroxy-2-methylimidazo[1,5-a]pyrimidine hydrochloride This compound was prepared from 3-chloroethyl-8-cyano-4-hydroxy-2-methylimidazo[1,5-a]pyrimidine and 4-[bis(4-fluorophenyl)methylene]piperidine according to the process described in Example 4, Stage B.

Yield: 47%.

Melting point: 287° C.

EXAMPLE 12

1-{2-[4-[(4-Fluorophenyl)phenylmethylene]-piperidino]ethyl}-4-(2-pyridylmethyl)-2,6-piperazinedione trihydrochloride This compound was prepared from 4-[(4-fluorophenyl)phenylmethylene]piperidine and 1-(2-chloroethyl)-4-(2-pyridylmethyl)-2,6-piperazinedione according to the process described in Example 6, Stage E.

Yield: 41%.

Melting point: 171° C.

EXAMPLE 13

8-Carbamoyl-4-hydroxy-3-{2-[(4-methylphenyl)-phenylmethylene]piperidino]ethyl}-2-methylimidazo[1,5-a]pyrimidine hydrochloride This compound was prepared from ethyl 2-acetyl4-{4-[(4-methylphenyl)phenylmethylene]-1-piperidyl}butyrate and 4-amino-5-carbamoyl imidazole hydrochloride according to the process described in Example 1.

Yield: 38%.

Melting point: 260° C.

EXAMPLE 14

1-{3-[4-fluorophenyl)methylene]piperidino]propyl}-4-(1-isoquinolyl)piperazine dihydrochloride Using the procedure described in Example 7, but 1-(2-pyrimidinyl)piperazine being replaced by 1-(1-isoquinolyl)piperazine, the product of the title is obtained.

EXAMPLE 15

1-{3-[4-[Bis(4-fluorophenyl)methylene]piperidino]-propyl}-4-(2-quinolyl)piperazine dihydrochloride Using the procedure described in Example 7, but 1-(2-pyrimidinyl)piperazine being replaced by 1-(2-quinolyl)piperazine, the product of the title is obtained.

EXAMPLE 16

1-{3-[4-[Bis(4-fluoromethyl)methylene]piperidino]-propyl}-4-(2-trifluoromethylbenzyl)piperazine Using the procedure described in Example 7, but 1-(2-pyrimidinyl)piperazine being replaced by 1-(2-trifluoromethylbenzyl)piperazine, the product of the title is obtained.

EXAMPLE 17

1-{3-[4-[Bis(4-fluorophenyl)methylene]piperidino]propyl}-4-(2-thiazolyl)piperazine dihydrochloride Using the procedure described in Example 7, but 1-(2-pyrimidinyl)piperazine being replaced by 1-(2-thiazolyl)piperazine, the product of the title is obtained.

EXAMPLE 18

1-{3-[4-[Bis(4-fluorophenyl)methylene]piperdino]propyl}-4-(4-methylthiazolyl)piperazine dihydrochloride Using the procedure described in Example 7, but 1-(2-pyrimidinyl)piperazine being replaced by 1-(4-methyl-2-thiazolyl)piperazine, the product of the title is obtained.

EXAMPLE 19

1-{3-[4-[Bis(4-fluorophenyl)methylene]piperidino]propyl}-4-(4-phenyl-2-thiazolyl)piperazine dihydrochloride Using the procedure described in Example 7, but 1-(2-pyrimidinyl)piperazine being replaced by 1-(4-phenyl-2-thiazolyl)piperazine, the product of the title is obtained.

EXAMPLE 20

1-{3-[4-[Bis(4-fluorophenyl)methylene]piperidino]propyl}-4-(4,5-dimethyl-2-thiazolyl)piperazine dihydrochloride Using the procedure described in Example 7, but 1-(2-pyrimidinyl)piperazine being replaced by 1-(4,5-dimethyl-2-thiazolyl)piperazine, the product of the title is obtained.

EXAMPLE 21

1-{3-[4-[Bis(4-fluorophenyl)methylene]piperidino]propyl}-4-(2-benzothiazolyl)piperazine dihydrochloride Using the procedure described in Example 7, but 1-(2-pyrimidinyl)piperazine being replaced by 1-(2-benzothiazolyl)piperazine, the product of the title is obtained.

EXAMPLE 22

3-{2-[4-[Bis(4-fluorophenyl)methylene]perhydro azepino ethyl}-8-carbamoyl-4-hydroxy-2-methylimidazo[1,5-a]pyrimidine hydrochloride

STAGE A 4-(N,N-Dimethylamino)butyronitrile 420 g of dimethylamine are added to a solution, heated to 80° C., of 400 g of 4-chlorobutyronitrile in 1200 ml of pure ethanol. After 12 hours under reflux, the solvent is concentrated, 3 liters of ethyl ether are then added and the precipitate formed is removed. The filtrate is concentrated and distilled at 12 mm Hg.

Proton nuclear magnetic resonance spectrum (200 MHz, solvent CDCl$_3$): 1.75 ppm, q, 2H; 2.25 ppm, s, 6H; 2.3-2.5 ppm, t+t, 2H+2H

STAGE B

2-[2-(N,N-Dimethylamino)ethyl]-5-chloropentanenitrile

A solution of 0.800 mol of the product obtained in the preceding stage is added to a solution, cooled to −85° C., of 0.800 mol of lithium diisopropylamide in 600 ml of tetrahydrofuran. The mixture is left for 20 minutes at −85° C. and 0.800 mol of pure 3-chloro-1-iodopropane is then added in the course of 5 minutes. The mixture is left stirring for one hour and then hydrolyzed at −80° C. with 500 ml of 3% strength acetic acid. The mixture is concentrated under vacuum, the residue is taken up in 250 ml of water, the product is extracted with dichloromethane and this extract is concentrated.

Yield: 90%,

Proton nuclear magnetic resonance spectrum (200 MHz, solvent CDCl$_3$): 1.6-2.1 ppm, m, 6H; 2.2 ppm, s, 6H; 2.3-2.6 ppm, m, 2H; 2.75 ppm, m, 1H; 3.6 ppm, t, 2H.

STAGE C

4-Cyano-1-methylperhydroazepine

A mixture of 140 g of the above product and 850 ml of nitrobenzene is brought to 120° C. for 12 hours and then cooled to 15° C., and 2 liters of ethyl ether are added. The precipitate obtained is filtered off and rinsed with ether. The product obtained is then mixed with one liter of decanol and the mixture is brought to reflux for two hours. It is then cooled and extracted four times with 500 ml of 1N hydrochloric acid, and this extract is neutralized with sodium hydroxide and extracted with dichloromethane. The oil is distilled under vacuum.

Yield: 70%.

Proton nuclear magnetic resonance spectrum (200 MHz, solvent CDCl$_3$): 1.5-2.2 ppm, m, 6H; 2.35 ppm, s, 3H; 2.5-3.0 ppm, m+m, 1H+4H

STAGE D

Ethyl 2-(1-methylperhydroazepin-4-yl)acetate

This compound was prepared from 4-cyano-1-methylperhydroazepine, the compound obtained in the preceding stage, according to the process described in Stage A of Example 8.

Yield: 90%.

Boiling point: 46°-48° C. at 0.03 mmHg.

STAGE E 1,1-Bis(4-fluorophenyl)-1-(1-methylperhydroazepin-4-yl)methanol

This compound was prepared from the product obtained in Stage D and according to the process described in Stage B of Example 8.

Yield: 85%.

Melting point: 109° C.

STAGE F

4-[Bis(4-fluorophenyl)methylene]-1-methylperhydroazepine

This compound was prepared from the product obtained in the preceding stage and according to the process described in Stage C of Example 8.

Yield: 75%.

Proton nuclear magnetic resonance spectrum (200 MHz, solvent CDCl$_3$): 1.8 ppm, m, 2H; 2.3-2.5 ppm, m+s, 2H+3H; 2.5-2.7 ppm, m, 6H; 6.9-7.15 ppm, m, 8H.

STAGE G

4-[Bis(4-fluorophenyl)methylene]-1-(ethoxycarbonyl)-perhydroazepine

This compound was prepared from 4-[bis(4-fluorophenyl)methylene]-1-methylperhydroazepine and according to the process described in Stage D of Example 8.

Yield: 95%.

STAGE H

4-[Bis(4-fluorophenyl)methylene]perhydroazepine

This compound was prepared from the product of the preceding stage and according to the process described in Stage E of Example 8.

Yield: 80%.

STAGE I

4-[Bis(4-fluorophenyl)methylene]-1-(chloroethyl)perhydroazepine hydrochloride

This compound was prepared from 4-[bis(4-fluorophenyl)methylene]perhydroazepine and according to the process described in Stage A of Example 1.

STAGE J

Ethyl 2-acetyl-4-{4-[bis(4-fluorophenyl)methylene]perhydroazepino}butyrate

This compound was prepared from the compound described in the preceding stage and according to the process described in Stage B of Example 1.

Yield: 38%.

Proton nuclear magnetic resonance spectrum (200 MHz, solvent CDCl$_3$): 1.3 ppm, t, 3H; 1.6–1.8 ppm, m, 2H; 1.9–2.7 ppm, m+s+m, 10H+3H+2H; 3.55 ppm, t, 1H; 4.15 ppm, q, 2H; 6.8–7.15 ppm, m, 8H.

STAGE K

3-{2-[4-Bis(4-fluorophenyl)methylene]perhydroazepino]ethyl}-8-carbamoyl-4-hydroxy-2-methylimidazo[1,5-a]pyrimidine hydrochloride was obtained from the ester prepared in the preceding stage and according to the process described in Stage C of Example 1.

Yield: 30%.

Melting point: >260° C.

EXAMPLE 23

3-{2-[3-[2,2-Bis(4-fluorophenyl)vinylene piperidino ethyl}-8-carbomoyl-4-hydroxy-2-methylimidazo[1,5-a]pyrimidine hydrochloride

STAGE A

Ethyl 2-(1-benzyl-3-piperidyl)acetate

Gaseous hydrogen chloride is added to the point of saturation to a solution, cooled to 5° C., of 34 g of (1-benzyl-3-piperidyl)acetonitrile (J. Pharm. Sciences, Vol. 55, No. 5, May 1966, p. 535) in 219 g of anhydrous ethanol and 350 ml of anhydrous ethyl ether. The mixture is then brought to reflux while gentle bubbling of hydrogen chloride is maintained. The mixture is concentrated, the residue is taken up in 150 ml of water, 300 ml of ethyl ether are added and the solution is neutralized using saturated sodium carbonate solution. After settling has taken place, the product is extracted twice with 200 ml of ethyl ether. The organic phase is dried over anhydrous sodium sulfate and concentrated. The oil obtained is chromatographed on 450 g of 70/230 mesh Merck 60 silica using a mixture of ethyl ether and hexane (50:50 V/V) as eluent.

Yield: 65%.

Proton nuclear magnetic resonance spectrum (200 MHz, solvent CDCl$_3$): 1–1.3 ppm, t, 3H; 0.7–3 ppm, m, 11H; 3.45 ppm, s, 2H; 3.9–4.3 ppm, g, 2H; 7.3 ppm, s, 5H.

STAGE B

1-Benzyl-3-[2,2-bis(4-fluorophenyl)-2-hydroxyethyl]-piperidine hydrochloride

A solution containing 58 g of 1-bromo-4-fluorobenzene in 100 ml of tetrahydrofuran is added under nitrogen to 7.41 g of magnesium suspended in 20 ml of tetrahydrofuran. The mixture is brought is brought to reflux for 2 hours and then cooled to 10° C., and a solution of 20 g of the compound obtained in the preceding stage, dissolved in 150 ml of tetrahydrofuran, is added. The mixture is brought to reflux for 10 hours and then hydrolyzed with 80 ml of saturated ammonium chloride solution at 0° C. The product is extracted 3 times with 200 ml of ethyl ether and the organic phases are dried over anhydrous sodium sulfate and concentrated. The monohydrochloride formed is precipitated in acetone and filtered off.

Yield: 80%.

Proton nuclear magnetic resonance spectrum (200 MHz, solvent CDCl$_3$+DMSO-d$_6$): 1.0–4.2 ppm, m+m+m, 2H+4H+7H; 6.7–7.7 ppm, m, 13H.

STAGE C

1-Benzyl-3-[2,2-bis(4-fluorophenyl)vinylene]piperidine

A mixture of 21 g of the product obtained in the preceding stage, 30 ml of concentrated hydrochloric acid and 100 ml of glacial acetic acid is brought to reflux for 3 hours. The mixture is concentrated, the residue is taken up in 1N sodium hydroxide and the product is extracted with dichloromethane. This organic phase is dried over anhydrous sodium sulfate and concentrated. The product is recrystallized in ethanol.

Yield: 70%.

Proton nuclear magnetic resonance spectrum (200 MHz, solvent CDCl$_3$): 1.5–3.5 ppm, m, 9H; 4–4.2 ppm, m, 2H; 5.5 ppm, d, 1H; 6.8–7.6 ppm, m, 13H.

STAGE D 1,1-Bis(4-fluorophenyl)-2-(3-piperidyl)vinyl

This compound was prepared from the product obtained in Stage C and according to the process described in Example 8, Stages D and E.

Yield: 77%.

Proton nuclear magnetic resonance spectrum (200 MHz, solvent DMSO-d$_6$): 1.3–1.9 ppm, m, 4H; 2.3–2.6 ppm, m, 1H; 2.6–2.9 ppm, m, 2H; 3–3.2 ppm, m, 2H; 5.9 ppm, d, 1H; 7–7.5 ppm, m, 8H.

STAGE E

Ethyl 2-acetyl-4-{3-[2,2-bis(4-fluorophenyl)vinylene]-piperidino}butyrate

This compound was prepared from 1,1-bis(4-fluorophenyl)-2-(3-piperidyl) vinyl according to the processes described in Stages A and B of Example 1.

Yield: 35%

STAGE H

3-{2-[3-[2,2Bis(4-fluorophenyl)vinylene]piperidino]ethyl}-8-carbamoyl-4-hydroxy-2-methylimidazo[1,5-a]pyrimidine hydrochloride was obtained from the compound described in the preceding stage according to the process described in Stage C of Example 1.

Yield: 25%.

Melting point: >260° C.

EXAMPLE 24

3-{3-[4-[2,2-Bis(4-fluorophenyl)vinylene]pyrrolidino]ethyl}-8-carbamoyl-4-hydroxy-2-methylimidazo[1,5-a]pyrimidine hydrochloride To prepare this compound, the procedure used is that described in Example 1, 4-[bis(4-fluorophenyl)methylene]piperidine being replaced by the compound obtained in Stage E of Example 8.

Yield: 30%.

Melting point: ≈265° C.

EXAMPLE 25

3-{2-[4-Bis(4-fluorophenyl)methylene]perhydroazepin-1-yl]ethyl}-2,4-dioxo-1,2,3,4-tetrahydroquinazoline hydrochloride A mixture of 7.5 g of 3-(2-chloroethyl)-2,4-dioxo-1,2,3,4-tetrahydroquinazoline, 10 g of 4-[bis(4-fluorophenyl)methylene]perhydroazepine, 3.4 g of sodium hydrogen carbonate and 100 ml of toluene is brought to reflux for 12 hours. The mixture is filtered and concentrated under vacuum. The oil obtained is purified by chromatography on 500 g of 70–230 mesh silica using a mixture of dichloromethane, methanol and ammonia solution (98.4:1.5:0.1 V/V) as eluent.

The corresponding hydrochloride is precipitated in acetone.

Yield: 60%.

Melting point: >260° C.

EXAMPLE 26

3-{2-[4-[Bis(4-fluorophenyl)methylene]perhydroazepin-1-yl]ethyl}-7-chloro-2,4-dioxo-1,2,3,4-tetrahydroquinazoline hydrochloride Using the procedure described in Example 25, but 3-(2-chloroethyl)-2,4-dioxo-1,2,3,4-tetrahydroquinazoline being replaced by 3-(2-chloroethyl)-7-chloro-2,4-dioxo-1,2,3,4-tetrahydroquinazoline, the product of the title is obtained.

Melting point: 260° C.

EXAMPLE 27

2-{2-[4-[Bis(4-fluorophenyl)methylene]piperidino]ethyl}-1,2-dihydro-1-oxophthalazine hydrochloride

STAGE A 1,2-Dihydro-1-oxo-2-(tetrahydropyran-2-ylethoxy)phthalazine

A solution of 41.5 g of potassium hydroxide in 53 ml of water is added to a solution of 61 g of 1,2-dihydro-1-oxophthalazine in 430 ml of dimethyl sulfoxide. After one hour, 130 g of 2-(2-bromoethoxy)tetrahydropyran are added rapidly and the mixture is left stirring at 20° C. for 48 hours. The solution obtained is then diluted with 1200 ml of water, the product is extracted with dichloromethane and the organic phase is dried over anhydrous sodium sulfate and concentrated.

Yield: 80%.

Proton nuclear magnetic resonance spectrum (200 MHz, solvent $CDCl_3$): 1.3–2 ppm, m, 6H; 3.3–4.8 ppm, m+m, 1H+6H; 7.6–7.9 ppm, m, 3H; 8.15 ppm, s, 1H; 8.4 ppm, m, 1H.

STAGE B 2-(2-Chloroethyl)-1,2-dihydro-1-oxophthalazine

A mixture of 90 g of the product obtained in Stage A, 600 ml of pure acetic acid, 300 ml of tetrahydrofuran and 150 ml of water is brought to 50° C. for 12 hours. It is concentrated under vacuum and the oil obtained is purified by chromatography on 1400 g of silica 60 (70–230 mesh) using a mixture of dichloromethane, methanol and ammonia solution (99:1:1 V/V) as eluent.

The oil obtained is mixed with 400 ml of chloroform and 35 g of thionyl chloride and heated to reflux for 3 hours. The mixture is concentrated and the solid obtained is recrystallized in isopropyl ether.

Yield: 45%.

Proton nuclear magnetic resonance spectrum (200 MHz, solvent $CDCl_3$): 3.95 ppm, t, 2H; 4.6 ppm, t, 2H; 7.15–7.9 ppm, m, 3H; 8.2 ppm, s, 1H; 8.4 ppm, m, 1H.

STAGE C

A mixture of 6.5 g of the compound obtained in the preceding stage, 8 g of 4-[bis(4-fluorophenyl)methylene]piperidine, 7.1 g of sodium hydrogen carbonate and 200 ml of toluene is brought to reflux for 24 hours. The mixture is concentrated and the oil obtained is purified by chromatography on 600 g of silica 60 (70–230 mesh) using a mixture of dichloromethane, methanol and ammonia solution (99:1:0.1 V/V) as eluent.

The hydrochloride of the product is then formed in acetone using hydrochloric acid.

Yield: 40%.

Melting point: 170°–172° C.

TABLE I

COMPOUNDS OF GENERAL FORMULA I

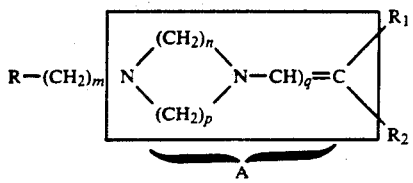

| Example No. | R | m | A | R₁ | R₂ | NMR SPECTRUM (SOLVENT) |
|---|---|---|---|---|---|---|
| 1 | H₃NCO-imidazo[pyrimidine with CH₃, OH] | 2 | −N⟩=C piperidine | 4-F-phenyl | 4-F-phenyl | ¹H NMR(DMSO-d₆)salt 2.6 ppm, s, 3H; 2.0–3.8 ppm, m, 12H; 6.9–7.7 ppm, m, 8H; 8.2 ppm, s, 1H. |
| 2 | tetrahydroisoquinoline-dione with −N− | 2 | −N⟩=C piperidine | 4-F-phenyl | phenyl | ¹H NMR(DMSO-d₆)salt 2.0–5.0 ppm, m, 19H; 7.0–7.6 ppm, m, 13H |
| 3 | H₃NCO-imidazo[pyrimidine with CH₃, OH] | 2 | −N⟩=C piperidine | phenyl | 4-F-phenyl | ¹H NMR(DMSO-d₆)salt 2.6 ppm, s, 3H; 2.0–3.8 ppm, m, 12H; 6.9–7.7 ppm, m, 9H; 8.2 ppm, s, 1H |
| 4 | NC-imidazo[pyrimidine with CH₃, OH] | 2 | −N⟩=C piperidine | phenyl | 4-F-phenyl | ¹H NMR(DMSO-d₆)salt 2.3–4.1 ppm, m, 15H; 7–7.75 ppm, m, 9H; 8.2 ppm, m, 1H |
| 5 | 2-F-benzyl-piperazinedione | 3 | −N⟩=C piperidine | phenyl | 4-F-phenyl | ¹H NMR(DMSO-d₆)salt 1.5–2.5 ppm, m, 6H; 2.5–4 ppm, m, +s+s, 8+2+2H; 6.8–7.5 ppm, m, 13H; 10.5–11.5 ppm, m, 1H exchangeable |
| 6 | 2-F-benzyl-piperazinedione | 3 | −N⟩=C piperidine | 2,2'-biphenyl | | ¹H NMR(DMSO-d₆)salt 1.6–2.4 ppm, m, 2H; 2.6–4 ppm, t+s+s+m, 2+2+4+10H; 6.8–8.1 ppm, m, 12H; 11–12 ppm, 1H exchangeable |
| 7 | −N-piperazinyl-pyrimidine | 3 | −N⟩=C piperidine | 4-F-phenyl | 4-F-phenyl | ¹H NMR(DMSO-d₆)salt 2–2.8 ppm, m, 2H; 2.8–4 ppm, m, 20H; 4.5–5 ppm, 1H, exchangeable; 6.7–7 ppm, t, 1H; 7.1–7.5 ppm, m, 8H; 8.5 ppm, d, 2H; 11–12.2 ppm, 1H exchangeable |
| 8 | 2-F-benzyl-piperazinedione | 3 | −N⟩C pyrrolidine | 4-F-phenyl | 4-F-phenyl | ¹H NMR(CDCl₃)base 1.5–2.1 ppm, m, 4H; 2.2–3.1 ppm, m, 7H; 3.45 ppm, s, 4H; 3.6–4.1 ppm, t+s, 2+2H; 5.9–6.2 ppm, d, 1H; 6.5–8 ppm, m, 12H |

TABLE I-continued

COMPOUNDS OF GENERAL FORMULA I

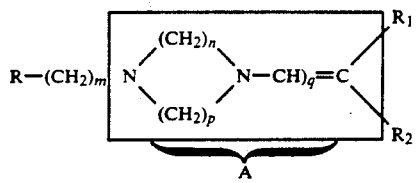

| EXAMPLE No. | R | m | A | R₁ | R₂ | NMR SPECTRUM (SOLVENT) |
|---|---|---|---|---|---|---|
| 9 | H₃NCO-imidazole-CH₃/OH substituted | 3 | -N-piperidine=C | phenyl | 4-F-phenyl | $^1$H NMR(DMSO-d$_6$)salt 1.7–2 ppm, m, 2H; 2.3–2.7 ppm, s+m, 3+2H; 2.7–3.2 ppm, m, 4H; 3.3–4 ppm, m, 6H; 6.9–7.5 ppm, m, 9H; 8.1 ppm, s, 1H; 10.3–10.6 ppm, 2H exchangeables; 11.5 ppm, 1H exchangeable |
| 10 | pyridin-2-yl-CH₂-N(piperazine-2,6-dione)-N— | 3 | -N-piperidine=C | phenyl | 4-F-phenyl | $^1$H NMR(D$_2$O)salt 1.5–4.0 ppm, s+m+m+m, 4+2+10+2H; 4.1 ppm, s, 2H; 6.5–7.8 ppm, m, 9H; 7.7–8.1 ppm, m, 2H; 8.3–8.7 ppm, m, 2H |
| 11 | NC-imidazole-CH₃/OH substituted | 2 | -N-piperidine=C | 4-F-phenyl | 4-F-phenyl | $^{13}$C NMR(DMSO-d$_6$)salt 17.2 ppm; 19.5 ppm; 27.8 ppm; 51.9 ppm; 53.4 ppm; 101.0 ppm; 111.5 ppm; 114.8 ppm; 115.1 ppm; 126.4 ppm; 130.4 ppm; 131.0 ppm; 135.5 ppm; 137.3 ppm; 137.7 ppm; 151.07 ppm; 155.5 ppm; 161.3 ppm |
| 12 | pyridin-2-yl-CH₂-N(piperazine-2,6-dione)-N— | 2 | -N-piperidine=C | phenyl | 4-F-phenyl | $^1$H NMR(DMSO-d$_6$)salt 2.4–3.9 ppm, m, 6+4H; 3.9 ppm, s, 4H; 3.9–4.3 ppm, m, 2H; 4.4 ppm, s, 2H; 7.1–7.6 ppm, m, 9H; 8–9.1 ppm, m, 4H; 10.5–11.6 ppm, 3H exchangeable |
| 13 | CONH₂-imidazole-CH₃/OH substituted | 2 | -N-piperidine=C | 4-CH₃-phenyl | phenyl | $^{13}$C NMR(DMSO-d$_6$)salt 17.3 ppm; 19.7 ppm; 20.5 ppm; 27.8 ppm; 52.2 ppm; 53.7 ppm; 101.1 ppm; 115.2 ppm; 123.4 ppm; 126.7 ppm; 128.2 ppm; 128.8 ppm; 128.9 ppm; 129.0 ppm; 132.6 ppm; 136.0 ppm; 137.9 ppm; 138.2 ppm; 141.3 ppm; 151.2 ppm; 155.8 ppm; 164.3 ppm |

TABLE I-continued

COMPOUNDS OF GENERAL FORMULA I

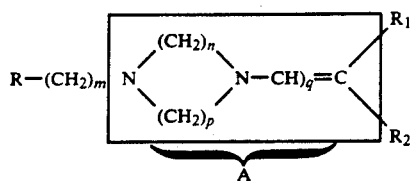

| EXAMPLE No. | R | m | A | R₁ | R₂ | NMR SPECTRUM (SOLVENT) |
|---|---|---|---|---|---|---|
| 22 | CONH₂-imidazole-pyrimidine(CH₃,OH) | 2 | azepane-C= | 4-F-phenyl | 4-F-phenyl | $^{13}C$ NMR(DMSO-$d_6$)salt 17.4 ppm; 19.9 ppm; 22.7 ppm; 28.5 ppm; 30.6 ppm; 52.5 ppm; 54.1 ppm; 54.2 ppm; 100.3 ppm; 114.9 ppm; 115.1 ppm; 115.2 ppm; 123.3 ppm; 130.6 ppm; 132.7 ppm; 135.2 ppm; 137.3 ppm; 138.2 ppm; 138.3 ppm; 151.1 ppm; 155.9 ppm; 159.7 ppm; 162.2 ppm; 164.3 ppm |
| 23 | H₃NCO-imidazole-pyrimidine(CH₃,OH) | 2 | piperidine-CH=C | 4-F-phenyl | 4-F-phenyl | $^{13}C$ NMR(DMSO-$d_6$)salt 17.2 ppm; 19.3 ppm; 21.9 ppm; 34.8 ppm; 51.2 ppm; 54.5 ppm; 54.6 ppm; 99.9 ppm; 115.5 ppm; 123.4 ppm; 128.8 ppm; 131.2 ppm; 132.5 ppm; 134.9 ppm; 137.6 ppm; 141.0 ppm; 151.4 ppm; 155.9 ppm; 160.2 ppm; 162.8 ppm; 164.3 ppm |
| 24 | CONH₂-imidazole-pyrimidine(CH₃,OH) | 2 | pyrrolidine-CH=C | 4-F-phenyl | 4-F-phenyl | $^{13}C$ NMR(DMSO-$d_6$)salt 17.2 ppm; 21.1 ppm; 29.8 ppm; 31.0 ppm; 52.2 ppm; 53.0 ppm; 57.0 ppm; 115.0 ppm; 115.4 ppm; 123.4 ppm; 128.6 ppm; 130.2 ppm; 132.5 ppm; 134.9 ppm; 137.6 ppm; 140.6 ppm; 151.7 ppm; 155.8 ppm; 159.8 t ppm; 163.0 ppm; 164.3 ppm |
| 25 | benzodiazepinedione | 2 | azepane-C= | 4-F-phenyl | 4-F-phenyl | RM $^1H$ NMR (DMSO-$d_6$)salt 1.95 ppm, m, 2H; 2.2-2.8 ppm, m, 4H; 3.0-3.7 ppm, m, 6H; 4.3 ppm, m, 2H; 7.0-7.3 ppm, m, 10H; 7.7 ppm, td, 1H; 7.95 ppm, m, 1H; 2H exchangeable 10.3 et 11.65 ppm |
| 26 | Cl-benzodiazepinedione | 2 | azepane-C= | 4-F-phenyl | 4-F-phenyl | $^1H$ NMR(DMSO-$d_6$)salt 1.9 ppm, m, 2H; 2.2-2.8 ppm, m, 4H; 3.0-3.7 ppm, m, 6H; 4.2 ppm, m, 2H; 7.05-7.30 ppm, m, 10H; 7.9 ppm, d, 1H; 2H exchangeable at 10.1 and 11.8 ppm |

TABLE I-continued
COMPOUNDS OF GENERAL FORMULA I

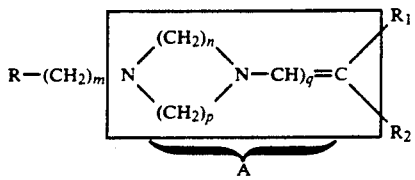

| X-AMPLE No. | R | m | A | R₁ | R₂ | NMR SPECTRUM (SOLVENT) |
|---|---|---|---|---|---|---|
| 27 | (2-formyl-phenyl-carbonyl-hydrazono group) | 2 | −N(piperidinylidene)=C | −C₆H₄−F (para) | −C₆H₄−F (para) | $^1$H NMR(CDCl$_3$)base 2.6 ppm, m, 2H; 2.85 ppm, m, 2H; 3.05 ppm, m, 2H; 3.5 ppm, t, 2H; 3.7 ppm, t, 2H; 4.8 ppm, t, 2H; 7.0 ppm, m, 8H; 7.6–7.9 ppm, m, 3H; 8.2 ppm, s, 1H; 8.4 ppm, dd, 1H |

PHARMACOLOGICAL STUDY

EXAMPLE 28

Histamine antagonism

Male albino guinea pigs (350–400 g) are subjected to a water diet for 18 hours before the test and anesthetized intraperitoneally with ethyl carbamate at a dose of 1.25 g/kg. A catheter is introduced into a carotid artery to measure the arterial blood pressure by means of a P23ID pressure cell connected to a Gould 2400® recorder. Another catheter is introduced into a jugular vein and is used for injecting the test compounds. The trachea is cannulated and the guinea pig is subjected to assisted respiration using a Havard respirator for small animals.

The guinea pig's temperature is maintained in the vicinity of 37° C. using a heating lamp. A needle inserted into the tracheal cannula is connected to a P50 pressure cell enabling the tracheal pressure to be recorded.

The guinea pigs are pretreated with d-tubocurarine (1 mg/kg i.v.). Histamine is then injected intravenously at a dose of 10 μg/kg. This dose induces bronchoconstriction and leads to an increase in the tracheal pressure. The histamine injections are repeated several times at 10-minute intervals until the response has stabilized. The compounds of the invention are then injected i.v. at cumulative doses, and the dose inhibiting 100% the increase in tracheal pressure caused by the injection of histamine (ID$_{100}$) is determined. The ID$_{100}$ of the compounds of the invention is between 20 and 250 μg/kg.

EXAMPLE 29

5-HT$_2$ antagonism

Male Sprague-Dawley rats (350–400 g) are anesthetized i.p. with pentobarbital (45 mg/kg). The trachea is cannulated and the animals are subjected to artificial respiration. The vagus nerves are sectioned. A catheter is placed in a carotid artery to record the arterial blood pressure. A second catheter is placed in the vein of the penis and is used for the injections. The animals' temperature is taken and is maintained at 37° C. The rats are pretreated with d-tubocurarine (1 mg/kg i.v.) and prazosin (1 mg/kg i.v.). 5-Hydroxytryptamine is injected i.v. at a dose of 100 μg/kg twice, separated by an interval of 10 minutes, so as to determine the rise in the systolic arterial blood pressure of each rat. 10 minutes later, the compounds of the invention are injected at the lowest dose and injection of 5-hydroxytryptamine is performed again 10 minutes later. 3 or 4 cumulative doses of the compounds of the invention are tested in the same manner. The percentages of the hypertensive response which are obtained at the different doses are calculated in order to determine the ID$_{50}$, the dose inhibiting the hypertensive response by 50%. The results of this study are presented in Table II.

TABLE II

| COMPOUND | ID$_{50}$ (μg/kg i.v.) |
|---|---|
| EXAMPLE 1 | 13.0 |
| EXAMPLE 3 | 24.0 |
| EXAMPLE 5 | 34.0 |
| EXAMPLE 6 | 39.0 |
| EXAMPLE 10 | 8.2 |
| EXAMPLE 13 | 27.0 |

EXAMPLE 30

α$_1$ antagonism

Male Sprague-Dawley rats (300–400 g) which have been subjected to a water diet are anesthetized with ethyl ether. A cannula is placed in the trachea. The spinal cord is destroyed by means of a steel rod and artificial respiration is instituted at once. The vagus nerves are sectioned. The carotid arteries are ligated and a catheter is placed in one of them to record the arterial blood pressure. A second catheter is placed in the vein of the penis and is used for the injections. The animals' temperature is taken and is maintained at 36° C. The rats are pretreated with a β-blocker (Tertatolol 100 μg/kg i.v.). Phenylephrine is injected at a dose of 4 μg/kg i.v. Two identical injections are performed, separated by an interval of 10 minutes. The compounds of the invention are injected at the lowest dose and injection of phenylephrine is performed again 10 minutes later. 3 or 4 cumulative doses of the compounds of the invention are tested in the same manner. The values for the percentage inhibition of the hypertensive response which are obtained at the different doses are calculated in order to determine the $ID_{50}$.

The results of this study are given in Table III.

TABLE III

| COMPOUND | $ID_{50}$ (μg/kg) |
|---|---|
| EXAMPLE 1 | >5000 |
| EXAMPLE 3 | >5000 |
| EXAMPLE 4 | >5000 |
| EXAMPLE 8 | 5300 |
| EXAMPLE 9 | >5000 |
| EXAMPLE 11 | >5000 |
| EXAMPLE 13 | 3050 |
| EXAMPLE 23 | >5000 |
| EXAMPLE 24 | >5000 |
| EXAMPLE 25 | 3050 |

EXAMPLE 31

5-HTP antagonism

4 Female Wistar rats (270±30 g), fasted for approximately 24 hours, are used. At the beginning of the test, they are administered the "control" solution or the solutions of the test compounds, and they are administered a solution of 5-hydroxytryptophan by gavage at a dose of 320 mg/kg. The animals are then placed under observation in transparent cages. Three parameters are assessed in the study: "forepaw treading", "flat body posture" and "head twitches". "Forepaw treading" corresponds to a pedaling motion of the forelimbs. This parameter is measured 80 minutes after the administration of 1,5-hydroxytryptophan and during a 10-minute observation period. This time is divided into 5-second periods and, if a movement is observed in this period, a score of 1 is assigned, the maximum score being 30 for the 10 minutes of observation and for each animal.

The parameter "head twitches" relates to the number of twitches of the head of the animals observed during 10 minutes. This parameter is assessed 90 minutes after the administration of 1,5-hydroxytryptophan and during a 10-minute period. "Flat body posture" corresponds to a flattening of the body which lasts for more than 10 minutes. This parameter is assessed throughout the period of observation of the animals. The results of these studies, which are presented in Tables IV to VI, demonstrate that the compounds of the invention are potent 5-HTP antagonists. The results presented in Table VI also demonstrate that the compounds of the invention are well absorbed orally, which constitutes a very considerable advantage in therapy.

TABLE IV

| 5-HTP antagonism: Compounds tested intraperitoneally | | | |
|---|---|---|---|
| | $ED_{50}$ (mg/kg) | | |
| COMPOUND | FPT* | FBP** | HT*** |
| EXAMPLE 1 | 2.5 | 0.08 | 0.63 |
| EXAMPLE 2 | 1.25 | 1.25 | 5 |

TABLE V

| 5-HTP antagonism: Compounds tested subcutaneously | | | |
|---|---|---|---|
| | $ED_{50}$ (mg/kg) | | |
| COMPOUND | FPT* | FBP** | HT*** |
| EXAMPLE 3 | 10 | 10 | 10 |
| EXAMPLE 7 | 5 | 5 | >10 |
| EXAMPLE 10 | 1.25 | 0.16 | 40 |

TABLE VI

| 5-HTP antagonism: Compounds tested orally | | | |
|---|---|---|---|
| | $ED_{50}$ (mg/kg) | | |
| COMPOUND | FPT* | FBP** | HT*** |
| EXAMPLE 1 | 10 | 0.16 | >10 |
| EXAMPLE 4 | 1.25 | 1.25 | 10 |
| EXAMPLE 6 | 5 | 2.5 | 5 |
| EXAMPLE 11 | 5 | 1.25 | 10 |

FPT* = forepaw treading
FBP** = flat body posture
HT*** = head twitches

EXAMPLE 32

Tablets containing 10 mg of 3-{2-[4-[bis(4-fluorophenyl)methylene]piperidino]ethyl}-8-carbamoyl-4-hydroxy-2-methylimidazo[1,5-a]pyrimidine hydrochloride [B.F.P.M.P.E.I.P.]

| | |
|---|---|
| B.F.P.M.P.E.I.P. | 10 g |
| Wheat starch | 100 g |
| Corn starch | 20 g |
| Magnesium stearate | 15 g |
| Talc | 20 g | per 1000 tablets containing 10 mg of active principle.

We claim:

1. A compound selected from those of formula I:

$$R-(CH_2)_m-N\begin{matrix}(CH_2)_n\\ \\(CH_2)_p\end{matrix}(-CH)_q=C\begin{matrix}R_1\\ \\R_2\end{matrix} \quad (I)$$

in which m is an integer from 2 to 4, n and p, which may be identical or different, are an integer equal to 1, 2 or 3, with the proviso that the sum of n and p is 3, q is 0 or 1, R is a 1,2,3,4-tetrahydro-2,4-dioxo-3-quinazolinyl radical, optionally substituted on the benzene ring with one or more halogen atoms or with alkyl radicals having 1 to 6 carbon atoms or alkoxy radicals having 1 to 6 carbon atoms, a 1,3,4,6,11,11a-hexahydro-1,3-dioxo-2H-pyrazino[1,2-b]isoquinol-2-yl radical, a 1,2-dihydro-1-oxo-2-phthalazinyl radical, optionally substituted on the benzene ring with one or more halogen atoms or with alkyl radicals having 1 to 6 carbon atoms or alkoxy radicals having 1 to 6 carbon atoms, a 2,6-dioxo-1-piperazinyl radical of formula W:

$$R_3-CH_2-N\begin{matrix}O\\ \| \\ \\ \\ \|\\O\end{matrix}N- \quad (W)$$

in which $R_3$ is a 2-pyridyl radical or a phenyl radical optionally substituted with one or more halogen atoms or alkyl or alkoxy radicals having 1 to 6 carbon atoms, a radical of formula Z:

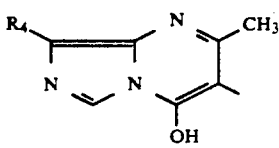 (Z)

in which $R_4$ is a carbamoyl radical, a cyano radical, a hydroxycarbonyl radical or an alkoxycarbonyl radical having 1 to 6 carbon atoms,
or a radical of formula Y:

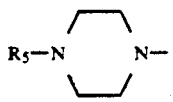 (Y)

in which $R_5$ is a 2-pyrimidinyl radical, a 1-isoquinolyl radical, a 2-quinolyl radical, a 2-pyridyl radical, a benzyl radical—optionally substituted with an alkyl radical having 1 to 6 carbon atoms containing one or more halogen atoms, a 2-thiazolyl radical—optionally substituted with one or more alkyl radicals having 1 to 6 carbon atoms or with a phenyl radical, or a 2-benzothiazolyl radical, and $R_1$ and $R_2$
either
identical or different, each are a phenyl radical substituted with one or more halogen atoms or with one or more alkyl or alkoxy radicals containing 1 to 6 carbon atoms, or $R_1$ is a phenyl radical and $R_2$ a 2-pyridyl radical, each of these two radicals being unsubstituted or substituted with one or more halogen atoms or with one or more alkyl or alkoxy radicals containing 1 to 6 carbon atoms, or $R_1$ and $R_2$, together with the carbon atom to which they are attached, form a fluorene radical, their stereoisomers and pharmaceutically-acceptable salts thereof.

2. A compound of claim 1 being 1-{3-[3-[2,2-bis(4-fluorophenyl)vinylene]-1 pyrrolidinyl]propyl}-4-(2-fluorobenzyl)-2,6-piperazinedione or a pharmaceutically-acceptable acid addition salt thereof.

3. A compound of claim 1 being 1-{3-[3-[2,2-bis(4-fluorophenyl)vinylene]-1 pyrrolidinyl]propyl}-4-(2-fluorobenzyl)-2,6-piperazinedione dihydrochloride.

4. A compound of claim 1 being 3-{3-[4-[2,2-bis(4-fluorophenyl)vinylene]pyrrolidino]ethyl}-8-carbamoyl-4-hydroxy-2methylimidazo[1,5-a]pyrimidine or a pharmaceutially-acceptable acid addition salt thereof.

5. A compound of claim 1 being 3-{3-[4-[2,2-bis(4-fluorophenyl)vinylene]pyrrolidino]ethyl}-8-carbamoyl-4-hydroxy-2-methylimidazo[1,5-a]pyrimidine hydrochloride.

6. A pharmaceutical composition containing, as active principle, a compound as claimed in claim 1, in combination or mixed with a pharmaceutically acceptable, non-toxic inert vehicle or excipient.

7. The pharmaceutical composition as claimed in claim 6, containing the active principle in an amount of 0.5 to 100 mg.

8. A method for the treatment of a disease requiring a serotonin antagonist comprising the step of administering to a living being suffering from such disease an effective serotonin-antagonistic amount of a compound of claim 1, or a pharmaceutical composition of claim 6.

9. The method of claim 8 wherein a pharmaceutical composition is administered, wherein the active compound is present in an amount of 0.5 to 100 mg.

10. A method of claim 8 wherein the compound is administered in the form of a pharmaceutical composition thereof in which it is combined with a pharmaceutically-acceptable vehicle or excipient.

* * * * *

UNITED STATES PATENT AND TRADEMARK OFFICE
CERTIFICATE OF CORRECTION

PATENT NO. : 5,079,249

DATED : Jan. 7, 1992

INVENTOR(S) : Gilbert Lavielle, Francis Colpaert, Michel Laubie

It is certified that error appears in the above-identified patent and that said Letters Patent is hereby corrected as shown below:

Title Page, [57] ABSTRACT, line 5 after Formula (I); "n and p" should read -- n and p is three, --.

Title Page, ABSTRACT, [57], 2nd column, Formula (Z);

Reads: 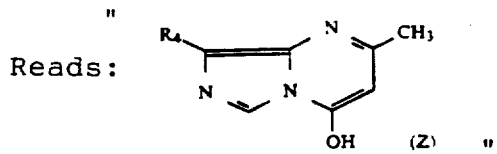    Should Read: 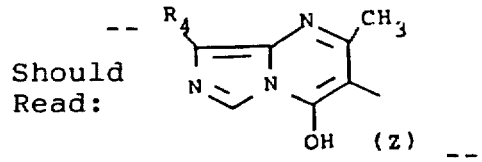

Column 3, approximately line 43, formula VI, first half of formula;

Reads: 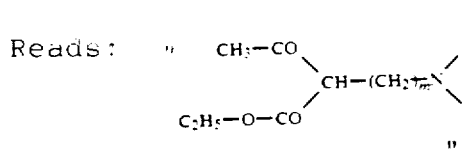    Should Read: 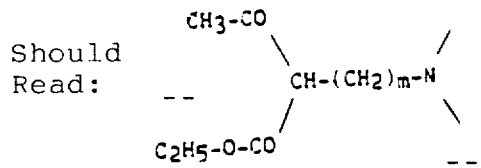

Column 5, line 62 and 63; "histamine-and serotoninan-tagonist" should read -- histamine and serotonin-antagonist --.

Column 6, lines 30, 31, and 32; delete "(LeBars, Neuronal Serotonin Eds. Osborne NN and Hamon M, John Wiley and Sons Ltd. NY., (1988), P. 171-229)" second occurrence.

Column 7, line 63; "4-{2-[4-]bis should read -- 4-{2-[4-[bis --.

Column 9, approximately line 55; "ar" should read -- at --.

Column 14, approximately line 38; "2-[(4-methylphenyl)-" should read -- 2-[4-[(4-methylphenyl)- --.

Column 14, approximately line 41; "2-acetyl4-" should read -- 2-acetyl-4- --.

Column 18, approximately line 10; "g," should read -- q, --.

Column 19, approximately line 15; "2Bis" should read -- 2-Bis --.

Column 19, approximately line 15; move the "e" at the end of the line to the beginning of the next line and insert before "thyl".

UNITED STATES PATENT AND TRADEMARK OFFICE
CERTIFICATE OF CORRECTION

PATENT NO. : 5,079,249

DATED : Jan. 7, 1992

INVENTOR(S) : Gilbert Lavielle, Francis Colpaert, Michel Laubie

It is certified that error appears in the above-identified patent and that said Letters Patent is hereby corrected as shown below:

Column 19, approximately line 26; move the "e" at the end of the line to the beginning of the next line and insert before "thyl".

Column 20, line 7; move the "e" at the end of the line to the beginning of the next line and insert before "thyl".

Columns 21 and 22, 23 and 24, 25 and 26, and 27 and 28 in Table I at the top, in "Compounds Of General Formula I", middle of formula; "N-CH)$_q$" should read -- (-CH)$_q$ -- in all four instances.

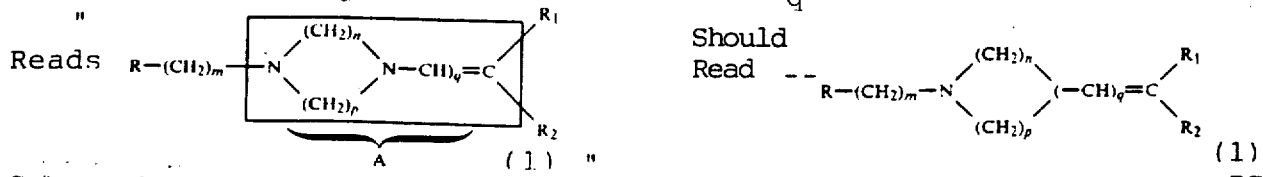

Columns 21, 23, 25, and 27, Table I, first column heading to the far left, first line; in each instance "X-" should read -- EX- --.

Columns 23, 24, Table I Continued, Example 10, last column, 4th line; "7.8" should read -- 7.3 --.

Columns 25, 26, Table I Continued, Example 23, last column, 3rd line, after "ppm;" first occurrence, and before "34.8", insert -- 28.2 ppm; --.

Column 31, approximately line 24; "atoms." should read -- atoms -, --.

Column 32, line 14; "2methylimidazo" should read -- 2-methylimidazo --.

Signed and Sealed this

Twenty-ninth Day of June, 1993

Attest:

MICHAEL K. KIRK

Attesting Officer     Acting Commissioner of Patents and Trademarks